United States Patent [19]
Shirahata et al.

[11] Patent Number: 5,264,636
[45] Date of Patent: Nov. 23, 1993

[54] PROCESS FOR PRODUCING HIGHLY PURE PHENOL

[75] Inventors: Tatsuo Shirahata; Tetsuo Imamura, both of Ichihara, Japan

[73] Assignee: Mitsui Petrochemical Industries, Ltd., Tokyo, Japan

[21] Appl. No.: 39,726

[22] Filed: Mar. 30, 1993

[30] Foreign Application Priority Data

Apr. 3, 1992 [JP] Japan .................................. 4-082200

[51] Int. Cl.$^5$ .............................................. C07C 37/70
[52] U.S. Cl. ..................................... 568/754; 568/798
[58] Field of Search ................................. 568/754, 798

[56] References Cited

FOREIGN PATENT DOCUMENTS 0134427 2/1979 Fed. Rep. of Germany ...... 568/754
865677 4/1961 United Kingdom ................ 568/754
1231991 12/1971 United Kingdom ................ 568/754

Primary Examiner—Werren B. Lone
Attorney, Agent, or Firm—Birch, Stewart, Kolasch & Birch

[57] ABSTRACT

A process for producing a highly pure phenol, in which a crude phenol obtained from an acid-decomposition product of cumene hydroperoxide and having an α-methylstyrene content of 15% by weight or less is catalytically treated with an acidic γ-alumina catalyst having a specific surface area of 80 to 400 m$^2$/g and an acid strength, according to Hammett's acidity function (Ho), of $3 \leq Ho \leq 6.8$, in order to convert aliphatic and aromatic carbonyl compounds contained in the crude phenol into high-boiling compounds without causing the substantial formation of a dimer of α-methylstyrene contained in the crude phenol, and then, a phenol and the so-formed high-boiling compounds were separated by distillation.

8 Claims, No Drawings

PROCESS FOR PRODUCING HIGHLY PURE PHENOL

BACKGROUND OF THE INVENTION

1. Field of the Invention

The present invention relates to a process for producing a highly pure phenol, which comprises of removing impurities contained in a crude phenol obtained from an acid-decomposition product of cumene hydroperoxide. More specifically, it relates to a process for producing a highly pure phenol, which comprises of converting impurities contained in the above crude phenol into high-boiling compounds without causing a substantial loss of useful substances contained in the crude phenol, and recovering a phenol by distillation.

2. Related Art

As an industrial process, there is known a process for producing a phenol in which cumene hydroperoxide obtained by oxidation of cumene is acid-decomposed. The acid-decomposition product obtained by this process contains cumene, phenol, α-methylstyrene and acetone as main components along with a small amount of by-products. Meanwhile, a phenol is used as a raw material for producing diphenylolpropane, polycarbonate, etc., and the phenol as a raw material for these is required to have a high purity.

As far as the phenol for the above use is concerned, the content of hydroxyacetone (HA) as one of the impurities is required to be 30 ppm or less, preferably 10 ppm or less, and the total amount of aliphatic and aromatic carbonyl compounds (total carbonyl amount) other than HA is required to be 100 ppm or less, preferably 50 ppm or less.

For obtaining a highly pure phenol satisfying the above-described quality, it is general practice to carry out the following treatment for removing impurities. That is, a crude phenol, which is obtained by removing a large part of the low-boiling substances such as acetone, cumene, water and α-methylstyrene and a large part of the high-boiling substances such as acetophenone and α-dimethylphenylcarbinol from a neutralized acid-decomposition product by fractional distillation, is further purified to remove aliphatic carbonyl compounds such as hydroxyacetone (HA) and aromatic carbonyl compound such as α-phenylpropionaldehyde.

In conventional methods for producing a highly pure phenol, for example, Japanese Patent Publication No. 11,664/1962 discloses a method in which a crude phenol (containing 200 ppm of hydroxyacetone) is catalytically treated with an active alumina catalyst at 360° C. to allow the hydroxyacetone to react with a phenol to convert it into 2-methylbenzofuran (2-MBF), and phenol. The 2-methylbenzofuran are separated from each other by steam distillation. Further, Japanese Patent Publication No. 1,289/1979 discloses a method using an active alumina for purifying crude cresols.

Further, Japanese Patent Publication No. 12,250/1967 discloses a method in which a crude phenol is catalytically treated with a silica-alumina catalyst at 150° to 250° C. to convert carbonyl compounds into other compounds, and they are separated from a phenol by steam distillation. Furthermore, British Patent 1,231,991 discloses a method in which a crude phenol containing no water is catalytically treated with an acidic ion-exchange resin catalyst at 80° to 150° C. to convert carbonyl compounds to other compounds, and they are separated from a phenol by steam distillation.

The above methods are all directed to a method in which impurities are converted to other compounds. The defect with these methods is that phenol and α-methyl styrene as useful components react with impurities or respectively undergo condensation to form cumylphenol or dimer of olefin and thus, the useful components are wasted.

SUMMARY OF THE INVENTION

It is a first object of the present invention to provide a process for producing a highly pure phenol, which permits the-selective conversion of impurities to be removed to other high-boiling compounds without entailing the substantial loss of useful components contained in a crude phenol obtained by acid-decomposition of cumene hydroperoxide.

It is a second object of the present invention to provide a practical process for producing a highly pure phenol satisfying the quality required as an industrial raw material from the above crude phenol.

DETAILED DISCUSSION

According to studies of the present inventors, the above objects and advantages of the present invention are achieved by catalytically treating the above crude phenol in the presence of an acidic γ-alumina having a specific surface area to be specified later and an acid strength to be specified later.

That is, according to the present invention, there is provided a process for producing a highly pure phenol from a crude phenol which is obtained from an acid-decomposition product of cumene hydroperoxide and has an α-methylstyrene content of 15% by weight or less, the process comprising:

(1) catalytically treating the above crude phenol in the presence of an acidic γ-alumina catalyst having a specific surface area of 80 to 400 m²/g and an acid strength, according to Hammett's acidity function (Ho), of $3 \leq Ho \leq 6.8$, in order to convert aliphatic and aromatic carbonyl compounds contained in the crude phenol into high-boiling compounds without causing the substantial formation of a dimer of α-methylstyrene contained in the crude phenol.

(2) recovering a phenol by distillation of a catalytic treatment product obtained in step (1).

The crude phenol as an object to be purified in the present invention refers to a crude phenol which is obtained by acid-decomposing cumene hydroperoxide obtained by oxidation of cumene, neutralizing the acid-decomposition product and removing a large part of the low-boiling substances such as acetone, ciamene, water low and α-methylstyrene and a large part of the high-boiling substances such as acetophenone and α-dimethylphenylcarbinol from the neutralized product by fractional distillation. The crude phenol contains phenol as a main component and α-dimethylstyrene in an amount of 15% by weight or less, preferably 0.05 to 10% by weight.

The above crude phenol contains, as impurities, aliphatic carbonyl compounds such as hydroxyacetone (HA) and others, aromatic carbonyl compounds such as α-phenylpropionaldehyde and others, and other compounds. In the process of the present invention, not only hydroxyacetone but also other impurities such as aliphatic and aromatic carbonyl compounds and others can be selectively converted to high-boiling compounds and easily removed.

The acidic γ-alumina used as a catalyst in the present invention Is an intermediate compound formed when aluminum hydroxide ($Al_2O_3 \cdot nH_2O$) is decomposed under heat, and it has a tetragonal crystal structure. This acidic γ-alumina is clearly distinguishable from an α-alumina having a trigonal crystal structure.

The acidic γ-alumina used in the present invention has a specific surface area of 80 to 400 $m^2/g$, preferably 150 to 300 $m^2/g$, and an acid strength, according to Hammett's acidity function (Ho), of $3 \leq Ho \leq 6.8$, preferably $3.3 \leq Ho \leq 6.8$. The Hammett's acidity function (Ho) is an index showing the acidity (proton donation capability) of a relatively highly concentrated acid, and a greater negative value of Ho shows greater proton donation capability and a higher acidity. The acidic γ-alumina used in the present invention has an acid strength of $3 \leq Ho \leq 6.8$, i.e., has a low acidity.

The Hammett's acidity function and its measurement method are explained in J. Am. Chem. Soc., 54 2721 (1932) and Physical Organic Chemistry, Chapter 9, McGrawHill Books Co., Inc., New York (1940).

In the present invention, the acidic γ-alumina having the above-specified specific surface area and acid strength may be used in the form of a powder, while it also may be used in the form of any one of general solid catalysts, e.g., particles, pellets, and the like.

In the process of the present invention, the aliphatic or aromatic carbonyl compounds contained in the crude phenol are converted to high-boiling compounds by bringing the crude phenol into contact with the above acidic γ-alumina. The crude phenol which is to be brought into contact, i.e., catalytically treated, with the γ-alumina may be in any one of a liquid phase and a gaseous phase. The catalytic treatment is carried out at a temperature of 40° C. or higher, preferably at a temperature between 150° and 300° C., under atmospheric pressure or elevated pressure. Although not specially limited, the time for the catalytic treatment is properly 1 to 60 minutes. In general, the catalytic treatment is preferably carried out at a high temperature under a high pressure for a short period of time, or at a low temperature under a low pressure for a long period of time.

The method of the catalytic treatment is not specially limited, and any method such as a batch method, a continuous method, etc., may be employed. However, it is industrially preferred to employ a method in which the crude phenol in a liquid or gaseous phase, particularly the vaporized crude phenol, is catalytically treated by passing the crude phenol through a layer packed with the catalyst. In this case, the crude phenol may be diluted with an inert diluent such as nitrogen and cumene. The layer packed with the catalyst may be a layer of a fluidized bed or fixed bed. When the crude phenol in a liquid phase or gaseous phase is flowed through the layer packed with the catalyst, the liquid hourly space velocity (LHSV) is properly 12 to 1 $hr^{-1}$.

Due to the contact with the catalyst, the aliphatic carbonyl compounds such as hydroxyacetone, the aromatic carbonyl compounds such as α-phenylpropionaldehyde and the other impurities, contained in the crude phenol, are converted to high-boiling compounds. In this catalytic treatment, the useful components such as phenol and α-dimethylstyrene remain almost intact. This is presumably because the above γ-alumina acting as the catalyst, has a proper specific surface area and a proper acid strength.

The impurities contained in the crude phenol have been converted to high-boiling compounds due to the catalytic treatment, and can therefore easily be separated by distillation, whereby a highly pure phenol can be obtained. The distillation can be carried out by any one of steam distillation, organic solvent extractive distillation or the like.

The steam distillation can be carried out, for example, by the method described in Japanese Laid-Open Patent Publication No. 20,239/1984, in which the crude phenol is distilled in the presence of water to separate the crude phenol into a mixture which comprises phenol containing impurities and water, and a phenol which is substantially free of impurities, and the mixture and the phenol substantially free of impurities are separately recovered. The above method is employed for producing phenol according to the cumene process, and is known per se.

The organic solvent extractive distillation can be carried out by a method using polyalkylene glycol or its ether as is described in Japanese Patent Publication No. 1258/1975.

When the above steam distillation or organic solvent extractive distillation is carried out, α-methylstyrene contained in the crude phenol can be nearly entirely removed.

According to the process of the present invention, a highly pure phenol having a remarkably decreased content of impurities typified by carbonyl compounds can be obtained by catalytically treating the crude phenol with the acidic γ-alumina and then distilling the so-treated product. The obtained highly pure phenol can meet with the quality requirements of a variety of starting materials. In particular, the contents of hydroxyacetone and other carbonyl compounds are sufficiently as low as required. The highly pure phenol obtained according to the process of the present invention may be further purified by other treatment as required.

PREFERRED EMBODIMENTS

The present invention will be explained more specifically by reference to Examples, in which various carbonyl compounds as impurities were quantitatively measured by gas chromatography, etc., to determine the conversions of the impurities before and after the treatment.

EXAMPLE 1

An acid-decomposition product of cumene hydroperoxide was neutralized and distilled to remove a most part of low-boiling substances such as acetone, water, cumene and α-dimethylstyrene and a most part of high-boiling substances such as acetophenone and α-dimethylcarbinol. The resultant crude phenol had a purity of 98% by weight or less and contained 0.3% by weight of hydroxyacetone (HA), I to 2% by weight of α-methylstyrene and 0.2% by weight (as a total carbonyl content calculated as mesityl oxide) of carbonyl compounds other than HA.

The above-obtained crude phenol in a vapor phase was allowed to pass a fixed bed packed with acidic γ-alumina catalyst having a specific surface area of 280 $m^2/g$ and an acidity function of $3.3 \leq Ho \leq 6.8$, at 280° C. at LHSV of 2 $hr^{-1}$. The resultant product was analyzed to show an HA content of 5 ppm or less and a total carbonyl content of 30 ppm or less. Further, the amount of formed 2-methylbenzofuran was only 10 mol % of HA, and the formation of neither a dimer of α-dimethylstyrene nor cumylphenol was found.

Water in an amount of 15% by weight was added to the crude phenol having an HA content of 15 ppm or less and a total carbonyl content of 30 ppm or less, obtained in the above, and the mixture was subjected to steam distillation under atmospheric pressure to distill off hydrocarbons such as α-methylstyrene containing 5% by weight of a phenol from a column top. A crude phenol aqueous solution having an α-dimethylstyrene content of only 5 ppm or less was obtained as a column bottom product. Then, the crude phenol was subjected to batch distillation under reduced pressure to obtain water and a purified phenol as a column top product. As a result, there was obtained a purified phenol having a total impurity content of 30 ppm or less, an HA content of 2 ppm or less, a total carbonyl content of 20 ppm, a solidifying point of 40.85° C., a hue (Hasen number) of 5 or less and a sulfonation coloring value of 95%.

The hue (Hasen number) of the phenol refers to a value determined by comparing the color of the above-obtained phenol with colors of standard solutions of ASTM (American Society for Testing and Materials). The sulfonation coloring value was determined as follows. 20 Milliliters of a sample phenol was warmed on a hot water bath at 45° C. for 10 minutes, and 20 ml of concentrated sulfuric acid was quickly mixed. Then, the mixture was allowed to stand at room temperature for 1 minute and in water for 5 minutes. Thereafter, the mixture was charged into a 20 mm cell, and measured for transmittance at 532 μm with a photoelectric colorimeter, and the measurement value is expressed by percentage. The greater the value is, the higher the phenol quality is. The total carbonyl content was analyzed as follows. The phenol was colored by adding 2,4-dinitrophenylhydrazine, and the color of the colored phenol was compared with standard color hues based on mesityl oxide to determine the total carbonyl content as a mesityl oxide.

EXAMPLE 2

The same acidic γ-alumina as that used in Example 1 was impregnated with an aqueous solution containing 5% by weight of ammonium fluoride, and dried under a nitrogen current to obtain an acidic γ-alumina having a fluorine content of 1.5% by weight. The so-obtained γ-alumina had a specific surface area of 240 m$^2$/g and an acidity function of $+4.0 \leq Ho \leq 6.8$. Then, the procedures of Example 1 were repeated except that the γ-alumina was replaced with the above-obtained acidic γ-alumina and that the LHSV was changed to 1 hr$^{-1}$. The resultant product was analyzed to show an HA content of 5 ppm or less and a total carbonyl content of 20 ppm or less. Further, the amount of formed 2-methylbenzofuran was 5 mol % of HA, and α-dimethylstyrene remained intact.

Then, diethylene glycol in the same amount as that of the crude phenol was added to the crude phenol, and the mixture was subjected to batch distillation under reduced pressure to obtain hydrocarbons and a purified phenol as a column top product. As a result, there was obtained a highly pure phenol having a total impurity content of 20 ppm, an HA content of 2 ppm or less and a total carbonyl content of 15 ppm. The so obtained phenol had a solidifying point of 40.85° C., a hue (Hasen number) of 5 or less and a sulfonation coloring value of 98%.

COMPARATIVE EXAMPLE 1

Example 1 was repeated except that the γ-alumina was replaced with a hydrogen-exchange mordenite type zeolite having an acidity function of $Ho \leq 8.2$. As a result, the amount of formed 2-methylbenzofuran was 70 mol % of HA, and 90% of α-methylstyrene was polycondensed or polymerized.

COMPARATIVE EXAMPLE 2

Example 1 was repeated except that the γ-alumina was replaced with cation-exchange resin (Amberlyst-15R) and that the treatment temperature was changed to 120° C. As a result, the amount of formed 2-methylbenzofuran was 90 mol % of HA, and the total amount of α-dimethylstyrene was polycondensed or polymerized.

COMPARATIVE EXAMPLE 3

Example 1 was repeated except that the alumina was replaced with a γ-alumina catalyst having a specific surface area of 92 m$^2$/g and an acidity function of $-3.0 \leq Ho \leq +1.5$. As a result, 90 mol % of hydroxyacetone was converted to 2-methylbenzofuran, or phenol was consumed. Further, 50% of α-methylstyrene was dimerized or converted to cumylphenol.

COMPARATIVE EXAMPLE 4

The crude phenol having an HA content of 0.3% by weight and a total carbonyl content of 0.2% by weight which was obtained in Example 1, was subjected to the same distillation as that of Example 2. As a result, the so-obtained phenol had a total impurity content of 2,100 ppm, an HA content of 1,800 ppm, a total carbonyl content of 1,500 ppm and a solidifying point of 40.7° C.

According to the present invention, aliphatic and aromatic carbonyl compounds can be converted to high-boiling compounds, while inhibiting the substantial loss of phenol and α-methylstyrene as useful components, by catalytically treating the crude phenol with an acidic γ-alumina catalyst having the specified specific surface area and the specified acid strength. As a result, phenol can be easily separated, and a highly pure phenol can be produced.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for producing a highly pure phenol from a crude phenol which is obtained from an acid-decomposition product of cumene hydroperoxide and has an α-methylstyrene content of 15% by weight or less, the process comprising:
   (1) catalytically treating the above crude phenol in the presence of an acidic γ-alumina catalyst having a specific surface area of 80 to 400 m$^2$/g and an acid strength, according to Hammett's acidity function (Ho), of $3 \leq Ho \leq 6.8$ to convert aliphatic and aromatic carbonyl compounds contained in the crude phenol into high-boiling compounds without causing the substantial formation of a dimer of α-dimethylstyrene contained in the crude phenol, and then, (2) recovering a phenol by distillation of a catalytic treatment product obtained in step (1).

2. A process according to claim 1, wherein the crude phenol is catalytically treated at a temperature between 150° and 300° C.

3. A process according to claim 1, wherein the crude phenol is catalytically treated for 1 to 60 minutes.

4. A process according to claim 1, wherein the acidic γ-alumina has an acid strength of $3.3 \leq Ho \leq 6.8$ according to acidity function Ho.

5. A process according to claim 1, wherein the acidic γ-alumina has a specific surface area of 150 to 300 m$^2$/g.

6. A process according to claim 1, wherein the crude phenol is in a gaseous phase and catalytically treated with the acidic γ-alumina.

7. A process according to claim 1, wherein the crude phenol is in a liquid phase and catalytically treated with the acidic γ-alumina.

8. A process according to claim 1, wherein the catalytic treatment product is recovered by steam distillation or organic solvent extractive distillation.

* * * * *